United States Patent [19]
Abel et al.

[11] Patent Number: 5,842,983
[45] Date of Patent: Dec. 1, 1998

[54] BIOSENSOR

[75] Inventors: Petra Abel, Friedberg; Wolfgang Allendörfer, Bad Homburg, both of Germany

[73] Assignee: Fresenius AG, Germany

[21] Appl. No.: 698,120

[22] Filed: Aug. 15, 1996

[30] Foreign Application Priority Data

Aug. 18, 1995 [DE] Germany ............... 195 30 376.8

[51] Int. Cl.⁶ ............... A61B 5/05; G01N 27/26
[52] U.S. Cl. ............... 600/345; 204/403; 204/415; 205/778; 435/14; 435/817
[58] Field of Search ............... 128/635; 204/403, 204/415; 205/778, 777.5; 435/14, 182, 817; 436/95, 904; 422/82.01, 82.02, 90, 98, 68.1

[56] References Cited

U.S. PATENT DOCUMENTS

| | | | |
|---|---|---|---|
| 4,970,145 | 11/1990 | Bennetto et al. | 435/14 |
| 5,089,112 | 2/1992 | Skotheim et al. | 128/635 |
| 5,227,042 | 7/1993 | Zawodzinski et al. | 204/403 |
| 5,286,364 | 2/1994 | Yacynych et al. | 204/403 |

*Primary Examiner*—Jennifer Bahr
*Assistant Examiner*—Eric F. Winakur
*Attorney, Agent, or Firm*—Omri M. Behr, Esq.

[57] ABSTRACT

Biosensor for amperometric measurements wherein the measuring electrode (34) is made of an electrically conductive carrier made of carbon which is saturated with a platinum metal in colloidal form wherein a lead-off contact (10) of vitreous carbon runs from the measuring electrode (34). The porous carrier (6) is saturated with an enzyme suitably glucose oxidase for the determination of glucose wherein the surface of the carrier (68) is protected against the environment by a membrane (70).

24 Claims, 4 Drawing Sheets

BIOSENSOR

BACKGROUND OF THE INVENTION

1. Field of the Invention

The invention is directed to a bio-sensor for the amperometric determination of a substrate dissolved in an aqueous solution, in particular blood, comprising an enzyme for the conversion of the substrate, a measuring electrode having a surface for a redox reaction of the reaction product of the substrate and an electrically conductive carbonaceous carrier and a metal of Group VIII of the periodic table deposited upon said electrically conductive carrier, wherein the electrically conductive carrier is bonded to or saturated in the enzyme containing solution, a semipermeable membrane which tightly encloses the measuring electrode including the electrically conducting carrier, and a lead-off contact which issues from the electrically conducting carrier.

2. Discussion of the Prior Art

Bio-sensors serve for the determination of substrates, which are catalytically converted by an enzyme provided in the bio-sensor into a reaction product which the bio-sensor determine qualitatively and quantitatively. Such enzyme electrodes are conventionally used for the determination of glucose in the blood, wherein the enzyme glucose oxidase is provided, which catalytically assists in the conversion of glucose into gluconolactone/gluconic acid and hydrogen peroxide. In the amperometry, the hydrogen peroxide is oxidized in the following manner:

$$H_2O_2 \rightarrow 2H^+ + 2e + O_2.$$

The electrons liberated at the electrodes are removed as an oxidation stream and, in a particular zone, are proportional to the glucose concentration.

The glucose bio-sensor system discussed above can readily be applied to other systems, for example the alcohol/alcohol oxidase, lactate/lactate oxidase, uric acids/uricase, hydrogen peroxide/catalase systems and the like.

The conventionally utilized measuring or working electrodes, which comprise an enzyme for the conversion of the substrate dissolved in water, operate at a reference potential of 600 mV and above, which however, in several measuring systems, has heretofore led to undesired corrosion and other undesired side reactions. Previously, attempts have been made to reduce this reference potential, in that the substrate reaction product is similarly, with the assistance of a catalyst, converted into a metabolite as is shown in the above-mentioned conversion equation.

In British Patent 2,191,003 (EP 0 247 850, U.S. Pat. No. 4,970,145) there is described a bio-sensor in the form of an enzyme electrode in which a metal of the platinum group is utilized in the working electrode. In order to achieve the maximum reactive surface, the platinum metal is uniformly distributed in colloidal form on the electrically conductive carrier. This carrier material is similarly finely divided, suitably as a carbon powder which is stabilized by means of a hydrophobic binder forming resin.

Such a working electrode produced in accordance with this method operates at high current densities per surface area unit and generally speaking, at an operating potential of 300–350 mV as opposed to the previously mentioned potential of 600–700 mV.

The enzymes are either adsorbed on this porous working electrode or covalently bound thereon, wherein the front surface of the working electrode is covered with a porous membrane which however is permeable with respect to the appropriate enzyme substrate.

Electrical contacts run from this known working electrode which are made of platinum, silver, and the like. It has however now been found that even an electrical contact of the conventionally utilized platinum does not guarantee a long operating life (maximum 1 month), since after such a time period, it becomes corroded so the entire electrode must be swapped out.

Also other materials such as gold or copper have proved themselves as unsatisfactory replacements of this electrode since they corrode in a few weeks.

Similar electrode arrangements are described in EP 470, 290, EP 136,362, EP 127,958, EP 197,747, EP 48,090, EP 359,831, U.S. Pat. No. 4,655,880, U.S. Pat. No. 4,950,379, PCT-WO 89/05454, DD 297,713 and U.S. Pat. No. 5,227,042.

In EP 0 470,290, the working electrode comprises a sensor material of vitreous carbon with which the enzyme layer is closely bound. Since one is not here concerned with a catalytically operative carrier, at a working potential of less than 600 mV, there are no effects in the glucose, glucose/oxidase electrode arrangement, so that there the previously mentioned undesired potentials arise.

SUMMARY OF THE INVENTION

The problem to be solved by the present invention therefore is to improve an electrode arrangement of the type discussed hereinabove so that it operates at the lowest possible working potential, that is to say, less than 500 mV and is, furthermore, stable over a substantial length of time, that is to say, does not show any corrosion effect.

The solution to this problem lies therein that the lead-off contact is made of vitreous carbon.

The utilization of vitreous carbon which is electroconductively connected with the working or measuring electrode, has the advantage that no corrosion factors are called into play during the life of the electrode, which is determined substantially solely by the enzyme activity. The effective life of the enzymes is between 4 to 6 months, that is to say, a time period in which no type of corrosive changes are demonstrated by the vitreous carbon surface. Only minimal or substantially negligible disturbance potentials occur in the electrode so that the entire measuring procedure is substantially simplified. This has the consequence that utilizing the electrode of the present invention, direct measurements can be carried out on undiluted whole blood which heretofore was not possible with continuous measurements of human blood. In addition to total blood, other aqueous body fluids such as serum, plasma, spit, dialysis fluids, electrolyte solutions, and the like may be utilized where the substrate to be examined is contained in such a solution and can be examined by a sensor in accordance with the present invention.

The bio-sensor in accordance with the present invention may be advantageously utilized for the determination of glucose wherein, as an enzyme in this case, glucose oxidase (GOD) is utilized. Nevertheless, other oxidoreductases may be utilized, to which for example belong lactate-oxidase, cholesteroloxidase, galactooxidase, as well as peroxide producing enzymes and combinations of such enzymes. Reference is also made to the previously mentioned substrate/oxidase systems, for example uric acid/uricase, ascorbic acid/ascorbate/oxidase, pyruvate/pyruvateoxidase.

The enzymes to be utilized can either be adsorbed on the electrically conductive carrier material or otherwise definitively bound covalently to this carrier by a chemical reaction, that is to say, immobilized thereon.

With respect to the carrier itself, reference is made to the disclosure of the previously mentioned U.S. Pat. No. 4 970 145, the disclosure of which is incorporated herein by reference.

The carrier material utilized in the present invention comprises a porous layer of carbon-containing particles which are bound together with a binder forming resin. The size of these particles ranges up to 50 nm.

The particles themselves comprise carbon or graphite powder which has a dense content of functional groups, i.e., carboxylate, or amino or sulphur containing groups on the surface thereof. Because of their very considerable surface area, these powders can very readily bind the previously mentioned enzymes.

Advantageously, prior to compaction, utilizing a binding material such a powder may be coated with a colloidal suspension of a group VIII metal up to 20 wt % based on the carbon carrier, so that there is advantageously provided on the carbon carrier, an even coating of platinum or palladium as a metal of the platinum group.

After mixing with the platinum containing material, the carbon carrier is mixed with a conventional hydrophobic resinous binding material and converted into predetermined form. Advantageously, there are utilized fluorine containing resins. Suitably those based on polytetrafluorethylene may be utilized as the resin containing binding materials, as is set forth in the previously mentioned patent text, to which reference is made herein.

The binding materials are utilized in amounts up to 70 wt %, however this weight percentage is not considered to be critical.

The binding materials should have a minimum oxygen permeability under atmospheric conditions of at least $2 \times 10^{-3}$ cm$^3$O$_2$/cm$^3$ with respect to the polymer.

Furthermore, the particle size of the colloidal platinum metal which is absorbed on the surface of the carbon powder should lie in the range of 1 to 3 nm.

Advantageously, the electrically conductive carrier mixture containing the platinum metal is formed as a film which may advantageously be fixed to a carbon film as carrier material.

Suitable enzyme electrode substrates are sold under the designation PACE by the company E-TEK (or Proto TEK) and are conventionally utilized as electro-catalytic gas diffusion electrodes in fuel cells.

As previously mentioned, the enzyme can be adsorbed on a carrier or however can be definitively immobilized thereon. In accordance with the present invention, the absorption of enzyme is then preferred when the surface of the thus treated carrier is protected with respect to the aqueous substance to be measured by a microporous semipermeable membrane. On the other hand of course, the enzyme can be rigidly affixed to the carrier by means of a physical or chemical immobilization process in a manner such that protection by the membrane is not necessary.

In the situation of simple absorption, the enzyme is provided in an aqueous solution or suspension wherein this solution is applied to the porous carrier. Such a film coated with enzymes can then be combined with the previously mentioned take-off contact.

On the other hand, the enzyme may be combined with the surface of the carrier by means of known immobilization techniques such as covalent binding with carbodiimide or glutaraldehyde, as again it is as set forth in the previously mentioned U.S. patent which again is incorporated herein by reference.

The electrical lead-off body or contact comprises vitreous carbon which is formed by the pyrolysis of polymers having three-dimensionally cross-linked structure. In the macro realm, the glass carbon has practically no pores. However, in its plural layers, there are numerous open volumes. It is extraordinarily corrosion resistant against acids and alkali, as well as to melting and only melts at about 550° C. under attack by oxygen or oxidative melts.

Further details with respect to vitreous carbon are set forth in Zeitschriftfar Werkstofftechnik 15 (1984) pages 331–338, which again is incorporated herein by reference. It is sold by Hoechst AG under the trademark Sigradur. Vitreous carbons which may be utilized in accordance with the present invention are sold in the form of planar, ring formed, rod formed, or disc formed electrodes for chemical analysis. Furthermore, the surface of the vitreous carbon may be mechanically worked, for example, annular ring grooves and bores may be worked into cylindrical bodies.

As far as is desired, the surface structure of glassy or vitreous carbon, may be activated by treatment at elevated temperatures, for example, at about 500° C. or chemically by reaction with nitric acid.

In accordance with the present invention, activated vitreous carbon is especially utilized in the measuring arrangement of the present invention for counter-electrodes, whereas for the lead-off contact in the working electrode there is, generally speaking, utilized non-activated vitreous carbon.

In this working electrode, there is utilized as take-off contact, a rod or cylindrical formed body whose front face serves as the carrier for the electrically conductive carrier for the platinum metal electrode. On its rearward end, there is provided a take-off wire which suitably is rigidly affixed in an axial boring of the vitreous carbon body and is introduced in an electrically conductive manner.

The working or measuring electrode in accordance with the present invention is advantageously utilized in the flow-through cells in the form of a 2- or 3-electrode arrangement.

In the 2-electrode arrangement, a counter-electrode simultaneously serves as a reference electrode whereas in the 3-electrode arrangement in addition to the counter-electrode, there is a reference electrode.

In a measuring cell of the present invention, it is preferred to utilize a 3-electrode arrangement in which in addition to the measuring electrode of the present invention, there is provided an Ag/AgCl electrode as reference electrode and which contains an activated vitreous carbon counter-electrode.

There may further be utilized sensors for temperature measurement or further electrodes or the correction of interfering substances such as bovine serum, albumin, and supplementary electrodes. The examples further explain the invention.

BRIEF DESCRIPTION OF THE DRAWINGS

There is shown.

DETAILED DESCRIPTION OF THE PREFERRED EMBODIMENTS

Figure 1:
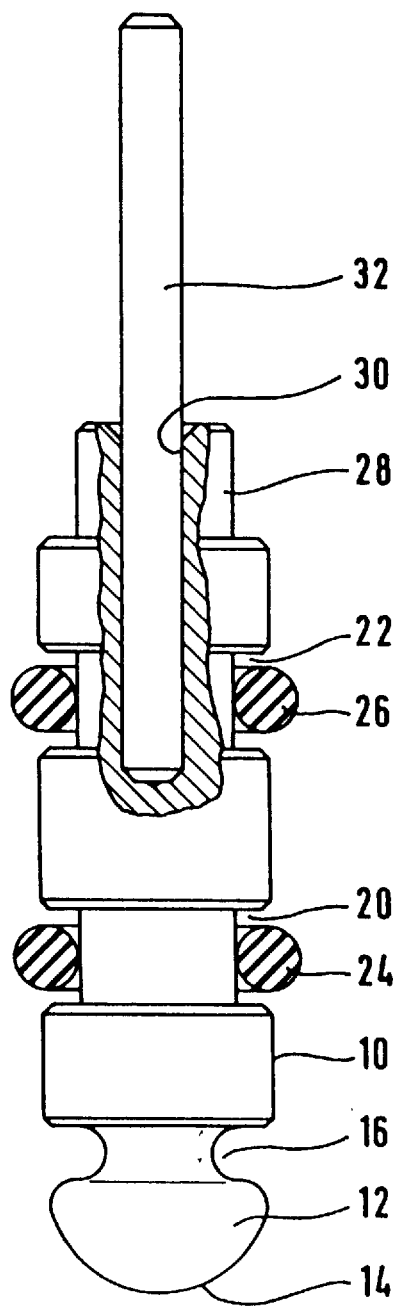
FIG. 1 is a side-elevational view of a vitreous carbon rod of the working electrode which is partially exposed in the region of the contact rod.

In FIG. 1 the electrode body 10 made of vitreous carbon is shown which has a substantially cylindrical structure. The front portion 12 of the electrode body 10 is shown in the embodiment of FIG. 1 as an outwardly protruding bulb which, as will later be discussed in detail with respect to the measuring cell of FIG. 2, facilitates the flow impact of the solution to be examined. Vicinal to this protrusion 14 is the first ring groove 16 in the electrode body in which a first O-ring as shown in FIG. 3 may be provided.

In addition to this first further ring grooves 20 and 22 are provided which are distributed over the electrode body in which further O-rings 24 and 26 may be inserted.

At the rearward end of the cylindrically formed electrode body 10, there is advantageously provided a cylindrically formed extension 28, which has a smaller diameter than that of the electrode body 10.

Furthermore, there is provided an axial bore 30 within the electrode body 10 into which is provided electrically conductive contact rod 32, suitably affixed thereto with an electrically conductive adhesive.

As is similarly shown in FIG. 3, the electrode body 10, the measuring electrode 34 and the reference electrode 36 are only differentiated in the structure in that the radius of curvature of the reference electrode 36 in the frontal section 38, is reduced.

As previously mentioned, the reference electrode is not made of carbon but rather of a silver/silver chloride rod containing the appropriate ring grooves 40 through 44, and O rings 46 through 50.

Figure 2:
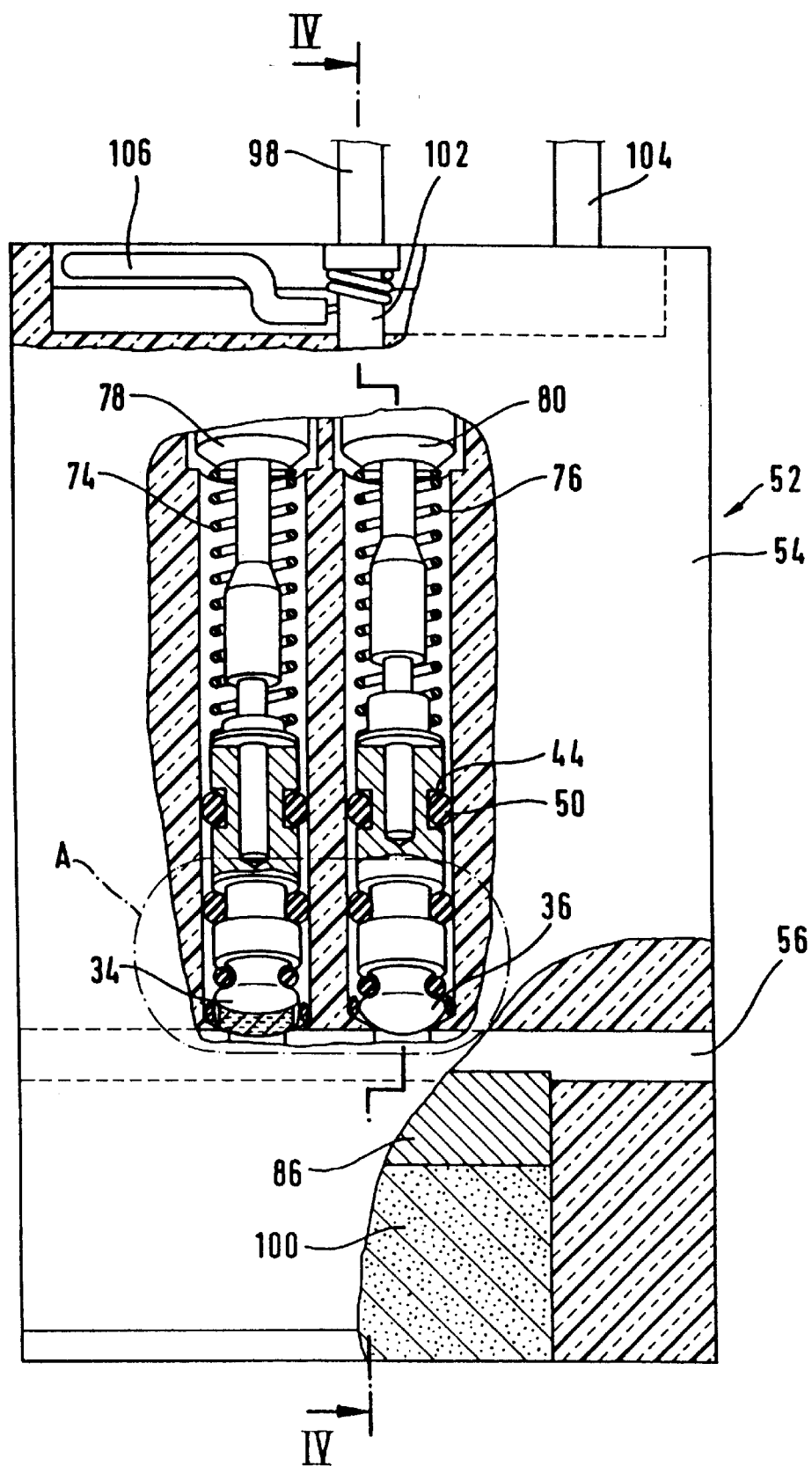
FIG. 2 is a 3-electrode containing measuring cell wherein the working electrode and the measuring electrode are shown in front elevation and in partial cross-section.
Figure 3:
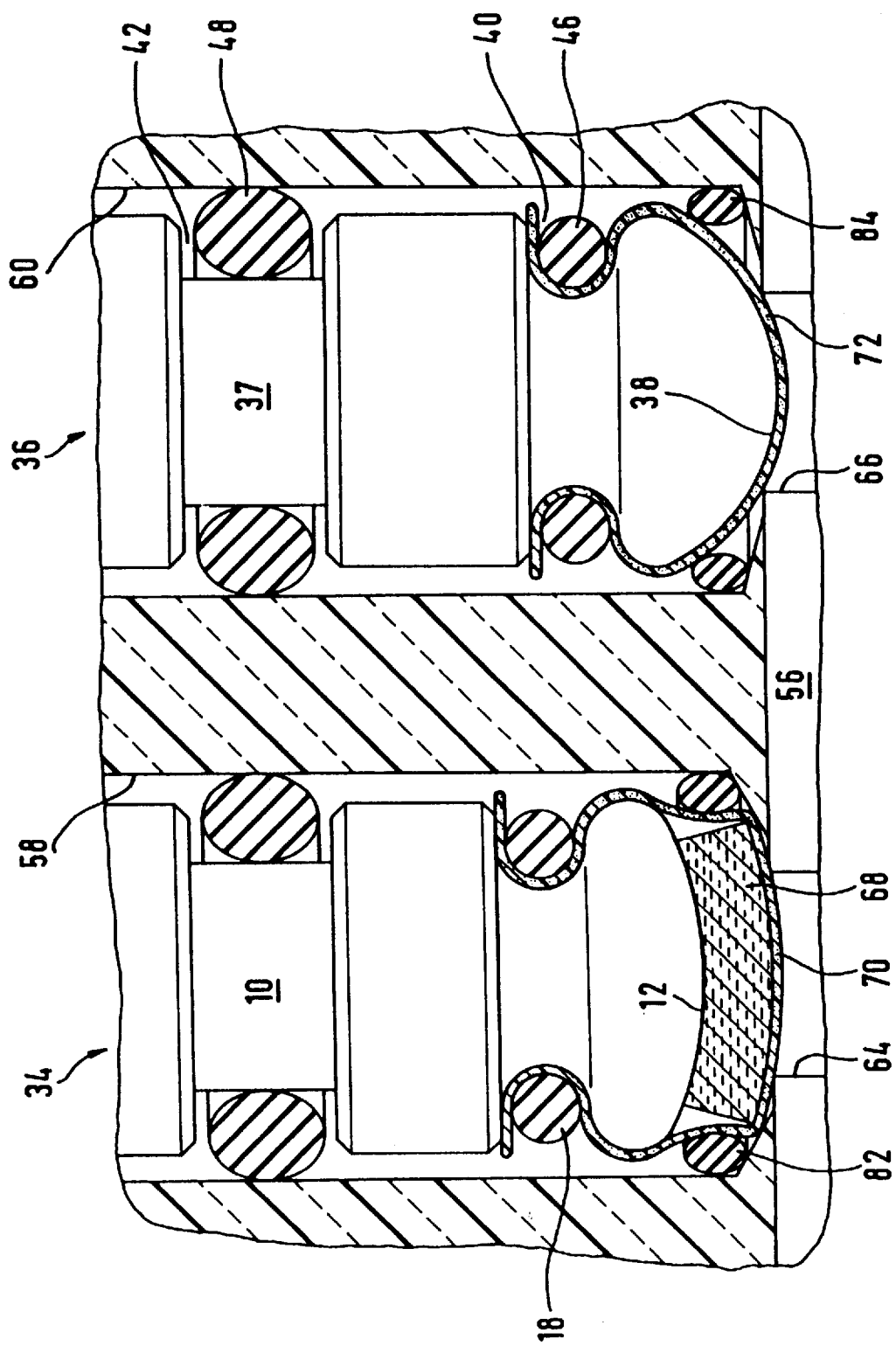
FIG. 3 is a magnified representation of detail A of FIG. 2 wherein the measuring electrode and the reference electrode are shown in cross-section, and FIG. 4 a cross-section through the measuring cell of FIG. 2 along the line IV—IV, wherein only the counter-electrode is provided.

In FIGS. 2 and 3 there is illustrated a measuring cell 52 which comprises an electrode block 54 generally made out of a transparent synthetic material such as acrylic glass, which has a measuring channel 56 therein which stretches transversely across the electrode block 54. Perpendicular thereto from above, there are the first, second and third borings in the electrode block 54 from which the first and the second boring 58 and 60 lead to the measuring channel 56, wherein the access openings 64 and 66, in boring 58 and 60, respectively, to measuring channel 56, have a narrower opening, that is to say, that their diameters are less than the diameter of the boring itself.

Furthermore, the diameters of the bores 58 and 60 are so provided that these are minimally larger than the diameter of the electrode body 10 of the measuring electrode 34 or the reference electrode 36. On the other hand however, the outer diameters of O-rings 24,26 as well as 48 and 50 are somewhat larger than the diameter of the bores 58 and 60, which leads to a radial sealing between the O-rings and the walls of the bores.

Further from FIG. 3, it will be seen that on the front face 12 of the working or measuring electrode 34, the previously mentioned electrically conductive carrier 68 is provided with a platinum group metal which is furthermore soaked in or saturated with an enzyme solution. Where glucose, for example, in blood, is to be determined with measuring electrode 34, the enzyme glucose oxidase is provided in carrier 68 which comprises an activated carbon film comprising colloidal platinum.

Around the front surface 12 of the electrode body 10 and on the front region of the provided PACE carrier 68, a semipermeable membrane 70 is provided in an enveloping manner which stretches rearwardly past the first ring groove 16 and is held in place in the groove by O-ring 18 and thus seals it against the environment. The enzyme solution provided in the PACE film 68 is thus located inside the membrane 70. Thus, the glucose solution is tightly enclosed in membrane 70 by the action of O-ring 18 and is thus protected from the influence of the environment, in particular the solution to be measured. The same applies to the reference electrode 36 whose front surface 38 is similarly protected by membrane 72 via the action of O-ring 46.

FIG. 2 illustrates the construction of the measuring electrodes 34 and 36 in the electrode block 54. As previously discussed, the electrodes are radially oriented within the bores 58 and 60 and tightly held therein and separated therefrom by O-rings 24 and 26 as well as 48 and 50 respectively. Furthermore, there is provided an axial biasing of electrodes 34 and 36 against the protrusion openings 64 and 66 provided by springs 74 and 76 which act in the rearward regions of electrode bodies 10 and 37, wherein segment 28 serves as a guide for spring 74. The bias of springs 74 and 76 within the bores 48 and 60 is caused by hollow plugs or screws 78 and 80 respectively as is shown in FIG. 2. In order to avoid damage to the front faces 12 and 34 and membranes 70 and 72 covering said frontal surfaces 12 and 38, vicinal to openings 64 and 66 in bores 60 and 62 respectively, there are provided O-rings 82 and 84 against which the outer edges of the frontal surfaces 12 and 38 are sealably spring biased wherein the pro-trusions of the front sides 12 and 38 protrude into measuring channel 56 so that the desired and sought after streaming conditions yield the optimal test probe contact. Because of the protrusion into the test channel, there is provided an arrangement which does not have a dead zone so that there is an efficient mode of operation of the probes free of lack of flow.

Figure 4:
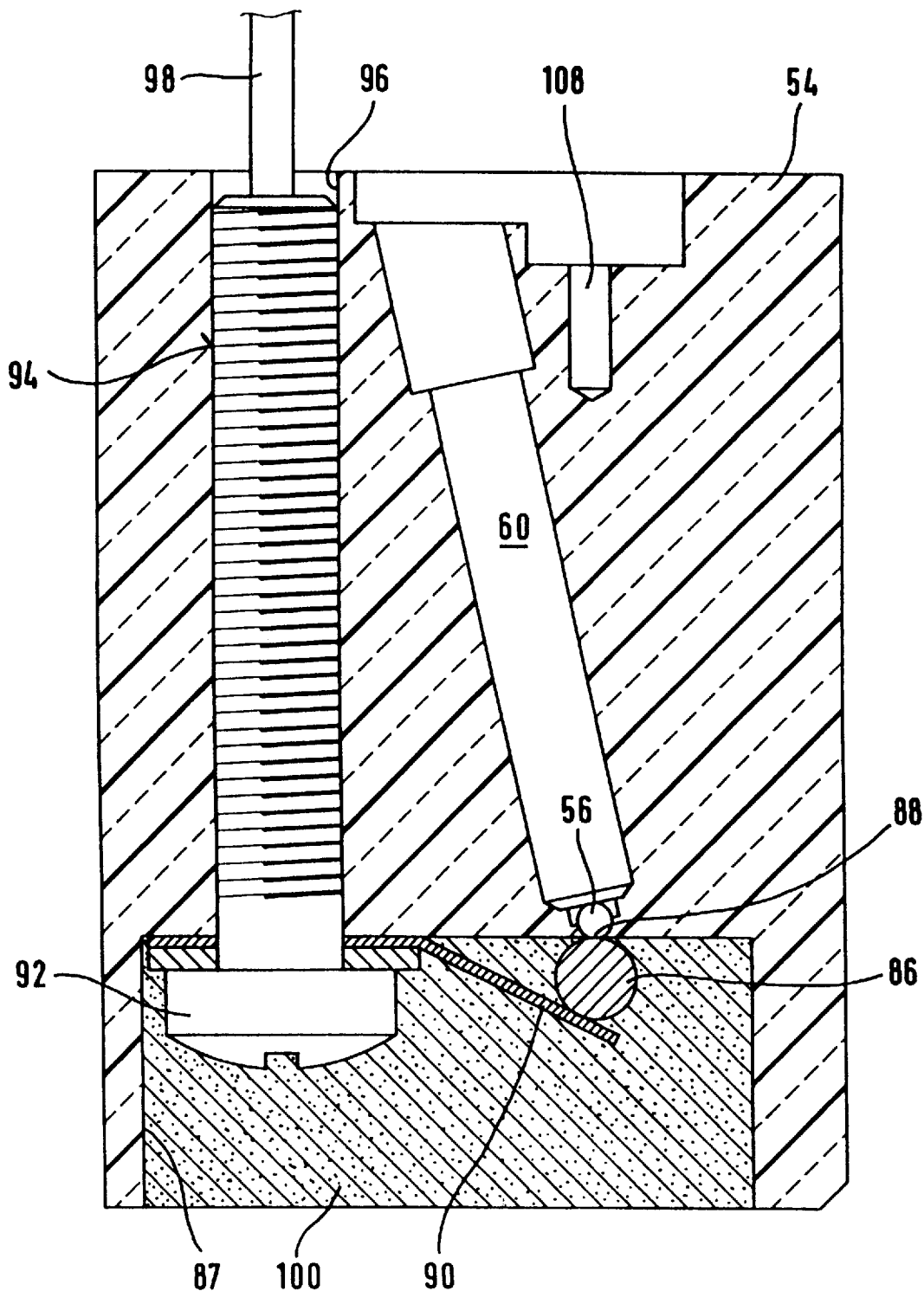

In accordance with FIG. 4 there is only shown the counter electrode 86 which as is shown in combination with the representation of FIG. 2, is provided in the form of a cylinder. The longitudinal axis of this counter electrode 86 runs parallel to the longitudinal axis of measuring channel 56 which has a correspondingly long slit 88 on its underside against which the outer surface of electrode 86 is pressed by means of spring element 90. This spring element is affixed to the electrode block 54 by means of a screw 92 for which purpose there is provided a vertical bore 94 in which the screw is affixed by means of a thread 96. Both the spring element 90 as well as the screw 92 are electrically conductive wherein the screw 92 can be outwardly connected to the measuring current surface by means of a contact rod 98.

As will be seen from FIG. 4, in the assembly mode, the counter electrode 86, the metallic spring element 90 and the screw 92 are introduced into the lower surface of the electrode block 54 in a substantially rectangular opening 87, which after assembly is sealed with a sealing resin 100. As previously mentioned the counter electrode 86 comprises, suitably, activated vitreous carbon.

As may be seen from FIG. 2 furthermore, contact rods 102 and 104 protrude from the electrode block 2 via electrical contact lines of which in FIG. 2 only line 106 (measuring electrode line) is shown with which the measuring electrode 34 as well as the reference electrode 36 are respectively connected.

The corresponding bore 108 for electrode rod 102 may be seen in FIG. 4.

EXAMPLE 1

A carbon film activated with colloidal platinum PACE is treated with a glucose/oxidase solution in such a manner that the film has a glucose/oxidase content of about 10 enzyme units per square millimeter. Thereafter, this film is utilized in the electrode arrangement of FIGS. 2 to 4.

This film is surrounded by a hydrophilic semipermeable membrane wherein the membrane has a mean pore diameter of approximately 30 nm. Solutions of different glucose concentrations in water/blood are led through measuring channel 56 whereby a current/potential curve (volt ampogram) is provided. The diffusion barrier current for a glucose concentration of 20 mmol/l lies in the order of 3 $\mu$A. Only very minimal disturbance potential or polarizations occur and these may be totally absent.

During the middle operating life of the electrode (about 6 months) which is determined solely by the consumption of enzyme, no corrosion is noted. Because of minimal probe removal and optimal probe contacts, clear disturbance-free signals are obtained. The measuring values are more exact and more reproducible than heretofore utilizing a 2-electrode system of the Ag/Pt type. Similarly, the linearity of the measuring signal at different measuring concentrations is improved and the measuring range itself is extended.

COMPARATIVE EXAMPLE 1

In place of the vitreous or glassy carbon in the measuring electrode, platinum itself is utilized in the electrode body 10 for current collection.

Even after a very short time, corrosion effects are noted through the usual additionally occurring battery potentials.

COMPARATIVE EXAMPLE 2

In place of the platinum coated carbon film (PACE) a carbon film which does not contain platinum is utilized. In all other respects Example 1 is repeated. With respect to the PACE film wherein the required potential to obtain the measuring effects is of the order of 330 mV. In this case, the measuring effects only occur at a level of 845 mV, wherein the measurement is accompanied by electrolytic disruption effects so that these electrodes can only be utilized in case of emergency.

We claim:

1. A biosensor for the amperometric determination of a substrate in an aqueous solution, comprising
    an enzyme for the conversion of the substrate to a substrate conversion product, a measuring electrode whose surface is suitable for a redox reaction of the substrate conversion product, said surface comprising a porous electrically conductive carrier of carbon having provided thereon a metal of group VIII in colloidal form, said electrically conductive carrier being saturated with an aqueous solution containing said enzyme,
    a lead-off contact connected to said electrically conducting carrier, wherein said lead-off contact is vitreous carbon, and
    a semi-permeable membrane tightly enclosing said electrically conducting carrier together with said enzyme solution and said vitreous carbon contact.

2. The biosensor in accordance with claim 1, wherein said vitreous carbon is activated.

3. The biosensor in accordance with claim 2, wherein the lead-off contact is a cylindrical unit having said measuring electrode upon its front face.

4. The biosensor in accordance with claim 3, wherein said front face has an outward curvature.

5. The biosensor in accordance with claim 3, wherein said cylindrical unit comprises a first annular groove.

6. The biosensor in accordance with claim 5, wherein said cylindrical unit comprises a further annular groove therein.

7. The biosensor in accordance with claim 5, wherein said cylindrical unit comprises further comprises an O-ring located in said first annular groove by means of which said membrane is fixable upon said cylindrical unit.

8. The biosensor in accordance with claim 7, further comprising an electrode block having a bore within which said cylindrical unit is located and comprises further O-rings located within said annular grooves by means of which the cylindrical unit is radially fixable within said bore.

9. The biosensor in accordance with claim 1, wherein the lead-off contact is a cylindrical unit having said measuring electrode upon its front face.

10. The biosensor in accordance with claim 9, wherein said front face has an outward curvature.

11. The biosensor in accordance with claim 9, wherein said cylindrical unit comprises a first annular groove.

12. The biosensor in accordance with claim 11, wherein said cylindrical unit comprises further annular ring grooves.

13. The biosensor in accordance with claim 11, wherein said cylindrical unit comprises further comprises an O-ring located in said first annular groove by means of which said membrane is fixable upon the said cylindrical unit.

14. The biosensor in accordance with claim 13, further comprising an electrode block having a bore within which said cylindrical unit is located and comprises further O-rings located within said annular grooves by means of which the cylindrical unit is radially fixable within said bore.

15. A measuring cell comprising an electrode block having a first and a second bore and a measuring channel therein, a biosensor in accordance with claim 1, being located in said first bore, a counter electrode being located in said block and a reference electrode being located in said second bore.

16. A measuring cell in accordance with claim 15 wherein the said first and said second bores are oriented substantially perpendicular to said measuring channel and open thereinto and the counter electrode forms at least a part of the wall of said measuring channel.

17. The measuring cell in accordance with claim 16, wherein the reference electrode is made of silver/silver chloride.

18. The measuring cell in accordance with claim 16, wherein the longitudinal axis of the counter electrode is substantially parallel to the longitudinal axis of the measuring channel and the counter electrode is pressed against a slit in the measuring channel provided in the electrode block.

19. The measuring cell in accordance with claim 15, wherein the counter electrode is made of vitreous carbon in the form of a cylinder.

20. The measuring cell in accordance with claim 19, wherein the vitreous carbon is activated.

21. The measuring cell in accordance with claim 20, wherein the longitudinal axis of the counter electrode is substantially parallel to the longitudinal axis of the measuring channel and the counter electrode is pressed against a slit in the measuring channel provided in the electrode block.

22. The measuring cell in accordance with claim 19, wherein the longitudinal axis of the counter electrode is substantially parallel to the longitudinal axis of the measuring channel and the counter electrode is pressed against a slit in the measuring channel provided in the electrode block.

23. The measuring cell in accordance with claim 15, wherein the reference electrode is made of silver/silver chloride.

24. The measuring cell in accordance with claim 15, wherein the longitudinal axis of the counter electrode is substantially parallel to the longitudinal axis of the measuring channel and the counter electrode is pressed against a slit in the measuring channel provided in the electrode block.

* * * * *